United States Patent [19]

Swaniger et al.

[11] Patent Number: 4,597,649
[45] Date of Patent: Jul. 1, 1986

[54] INFORMATION DISPLAY APPARATUS FOR OPHTHALMIC SLIT LAMPS

[75] Inventors: James R. Swaniger, Costa Mesa, Calif.; Roger F. Steinert; Carmen A. Puliafito, both of Boston, Mass.

[73] Assignee: American Hospital Supply Corporation, Evanston, Ill.

[21] Appl. No.: 546,501

[22] Filed: Oct. 28, 1983

[51] Int. Cl.⁴ ............................................. A61B 3/10
[52] U.S. Cl. ..................................... 351/214; 351/205
[58] Field of Search .............. 351/205, 212, 214, 425; 128/303.1, 395, 396, 397, 398

[56] References Cited

U.S. PATENT DOCUMENTS

| | | | |
|---|---|---|---|
| 2,110,330 | 3/1938 | Freeman | 351/212 |
| 3,091,167 | 5/1963 | Estes | 95/64 |
| 3,703,176 | 11/1972 | Vassiliadis et al. | 128/395 |
| 4,227,780 | 10/1980 | Ohta et al. | 351/208 |

FOREIGN PATENT DOCUMENTS 0030210 11/1980 European Pat. Off. .
8401110 3/1984 PCT Int'l Appl. .

Primary Examiner—John K. Corbin
Assistant Examiner—P. Dzierzynski
Attorney, Agent, or Firm—Weissenberger and Peterson

[57] ABSTRACT

A slit lamp with surgical laser capability includes an x-y table. An optical micrometer, readily retrofittable onto existing slit lamps, is mounted on the x-y table to measure table displacement in the y direction. The measuring electronics are resettable to allow the operator to select any y position from which the displacement is to be algebraically measured. Compact display optics are retrofittably mounted on the ocular assembly of the slit lamp between the collimator and the eyepiece to insert a reduced image of an LED indicator displaying the measured data into the periphery of the ophthalmic image seen through the eyepiece. An LCD indicator displaying the same data is mounted on the x-y table to allow positioning of the table without looking into the eyepiece. The LED indicator lends itself to display of laser operational data in addition to positional data.

7 Claims, 7 Drawing Figures

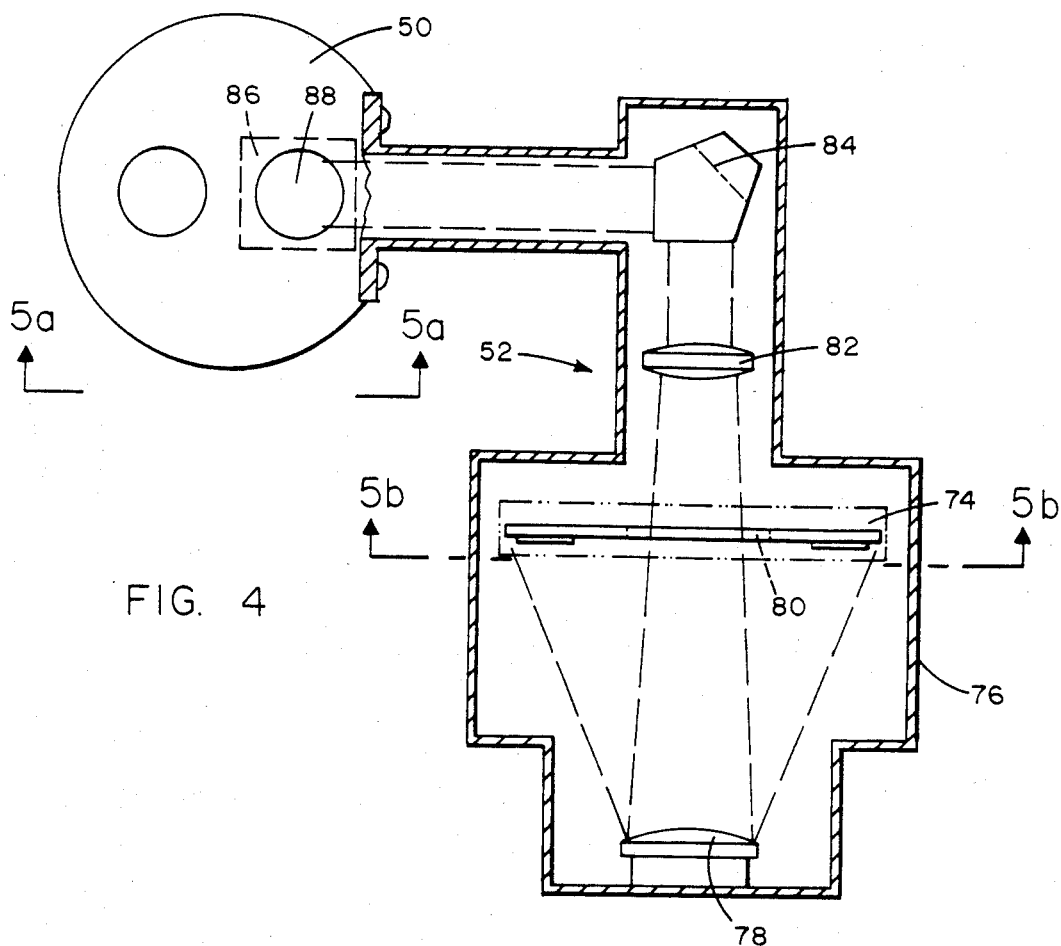
FIG. 4
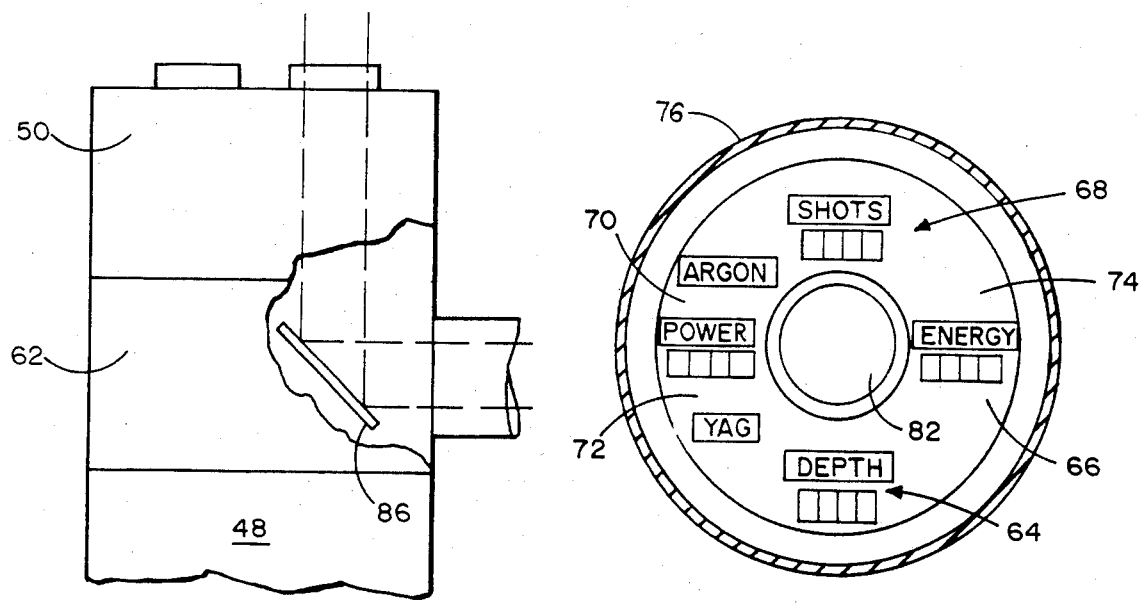
FIG. 5a
FIG. 5b

INFORMATION DISPLAY APPARATUS FOR OPHTHALMIC SLIT LAMPS

BACKGROUND OF THE INVENTION

A slit lamp with laser capability for ophthalmic surgery is disclosed in copending application Ser. No. 417,689, filed Sept. 13, 1982 and entitled "Instrument for Ophthalmic Laser Surgery". The slit lamp of that application is mounted on an x-y table so that the whole slit lamp assembly can be moved toward and away from the patient's eye as well as sideways by moving the x-y table in the desired directions. The movement capability in the y direction allows the surgeon to focus the laser beam at various depths within the patient's eye. The focusing is done with the aid of a benign aiming laser and is normally done empirically by the surgeon while observing the patient's eye.

For greater accuracy and improved efficiency, it would be desirable for the surgeon to be able to position the table at a particular point or along a particular line repetitively and without the need for careful empirical refocusing, as well as to be able to continuously observe an accurate measurement of the table's movement (and other relevant data) while observing the patient's eye.

SUMMARY OF THE INVENTION

The invention fulfills the above-described need by providing, within the field of view of the surgeon while observing the patient's eye, a numerical indication of the table's displacement from a selectable reference point. More generally, the invention provides a head-up display for the surgeon of various types of relevant data. The inventive device is easily retrofittable into existing slit lamps by the addition of an optical micrometer to the table structure and the addition of a beam-splitting display optic between the eyepiece and the collimator of the slit lamp.

The digital depth information supplied by the optical micrometer may also be displayed on a separate display mounted on the table surface so that the initial positioning of the table may be accomplished without any observation of the patient's eye.

It is therefore an object of this invention to provide visual data to the surgeon during his observation of the patient's eye in the slit lamp.

It is another object of the invention to provide numerical micrometer information for the positioning of the slit lamp table from any operator-determinable reference point.

It is a further object of the invention to provide micrometer information readable both while observing the patient's eye and while not doing so.

BRIEF DESCRIPTION OF THE DRAWINGS

FIG. 4 is a vertical section of the data display optics;

FIG. 5a is an inverted plan view along line 5a—5a of FIG. 4;

FIG. 5b is an inverted plan view along line 5b—5b of FIG. 4; and

DESCRIPTION OF THE PREFERRED EMBODIMENT

Figure 1:
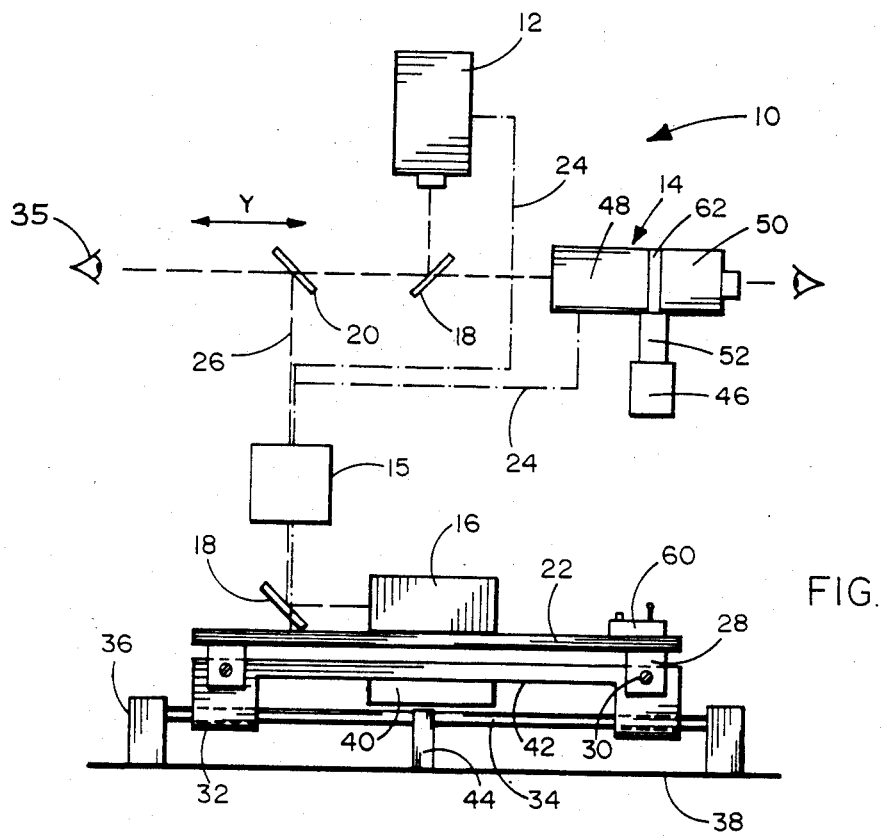
FIG. 1 is a schematic diagram illustrating the arrangement of the major components of a typical surgical slit lamp using the apparatus of this invention.

Referring first to FIG. 1, the surgical slit lamp 10 (such as, for example, the slit lamp described in the aforementioned copending application) conventionally consists of a light source 12, an ocular assembly 14, beam shaping optics 15, a laser 16, and appropriate mirrors 18 and beam splitters 20.

All of the foregoing components are mounted on an x-y table 22 as schematically indicated by dot-dash lines 24. The light source 12 and the ocular assembly 14 are pivotable about an axis coincident with the vertical portion of the laser beam 26.

The x-y table 22 is mounted on brackets 28 which slide on rails 30 for movement in the x direction (i.e. into and out of the paper in FIG. 1). The rails 30 are in turn supported by brackets 32 which slide on rails 34 for movement of the table 22 in the y direction (i.e. right to left in FIG. 1). Movement of the table 22 in the y direction causes the focal plane of the laser beam 26 to move from the front to the back of the patient's eye 35 to permit surgery on various parts of the eye. The rails 34 are secured to brackets 36 which are attached to a fixed surface 38.

In accordance with the invention, an optical micrometer 40 is mounted on the carriage 42 which connects the brackets 32 and is movable only in the y direction. The cursor 44 of the optical micrometer 40 is mounted in a fixed position with respect to the fixed surface 38 so as to move lengthwise with respect to the micrometer 42 when the carriage 40 is moved in the y direction. The indications produced by the micrometer 40 through its associated electronics (FIG. 6) are applied to a display unit 46. The display unit 46 is mounted on the ocular assembly 14 between the collimator 48 and the eyepiece 50. An optical reducer 52 is provided to translate the relatively large LED display into a relatively small image around the periphery of the ophthalmologic image seen through the eyepiece 50.

Figure 2:
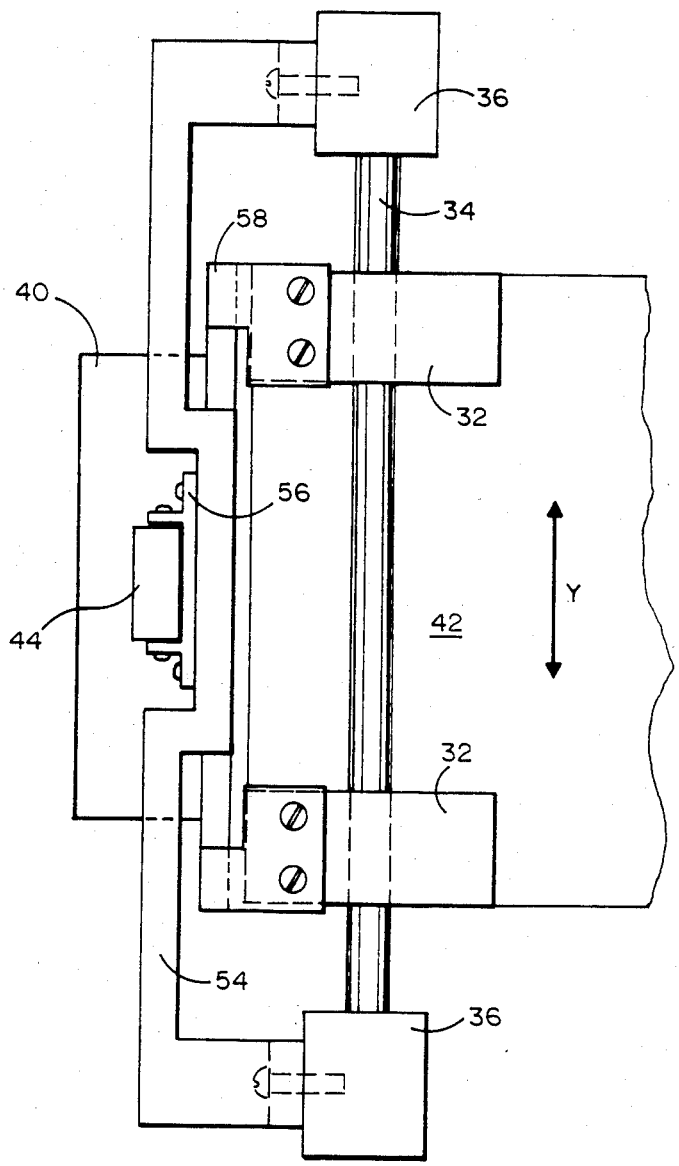
FIG. 2 is a fragmentary plan view of the x-y table mechanism with the optical micrometer attached.
Figure 3:
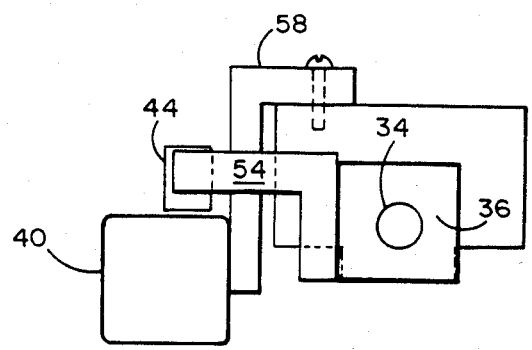
FIG. 3 is an end elevation of the mechanism of FIG. 2.

Referring now to FIGS. 2 and 3, the carriage 42 is shown with its bearing blocks 32 slidably mounted on rail 34. The ends of rail 34 are secured in the fixed brackets 36 to which a cursor support 54 is fixedly mounted. The cursor support 54 in turn carries a mounting bracket 56 on which the cursor 44 is mounted.

The carriage 42 has an extension 58 mounted thereon, which supports the optical micrometer 40 so that its longitudinal axis lies in the y direction.

The optical micrometer 40 is of conventional construction. An appropriate device of this type is manufactured by Teledyne Gurley. With the aid of conventional interpretive electronics, the optical micrometer 40 provides indications of cursor travel from one point to another with an accuracy of 1/100 cm.

A digital indication of the travel of cursor 44 (or rather of the micrometer 40 since it is the moving element) may advantageously be displayed both on a control console 60 mounted on the surface of table 22, and in the display optics 46. The former allows the surgeon to accurately position the table 22 without observing the patient, while the latter enables him to monitor movement of the table 22 during his observation of the patient's eye.

FIGS. 4 and 5 illustrate the functioning of the display optics 46 in conjunction with the reducer 52 and beam splitter ring 62. LED indicators such as y-direction depth indicator 64, energy level indicator 66, beam width indicator 68, and laser activation indicators 70, 72 are preferably disposed around the periphery of an indicator board 74. The indicator board 74 is rotatably mounted within the drum 76 so that it may be rotated by proper alignment of the image in the eyepiece 50.

The image of the indicator board 74 is reduced by reflection from a convex reflector 78 and is conveyed through an opening 80 in the center of board 74 to a movable focusing optic 82. The resulting collimated image is then reflected at right angles in a pentaprism 84 toward the beam splitter ring 62. The beam splitter ring 62 can be interposed between the collimator 48 and the eyepiece 50 of the ocular assembly 14 without interference because the left and right images are collimated along parallel lines between the collimator 48 and the eyepiece 50. A beam splitter 86 is interposed in the path of the image for one of the eyes (shown as the right eye 88) so as to produce a luminous image of the display data around the periphery of the ophthalmologic image seen through the eye 88. Because the board 74 is in darkness, its own image does not interfere with the observation of the patient's eye.

The folded optics contained within the drum 76 provide a means of using relatively large display components with a minimum requirement of bulk in the display optics. This is important because the display optics are eccentrically supported by the ocular assembly 14.

Figure 6:
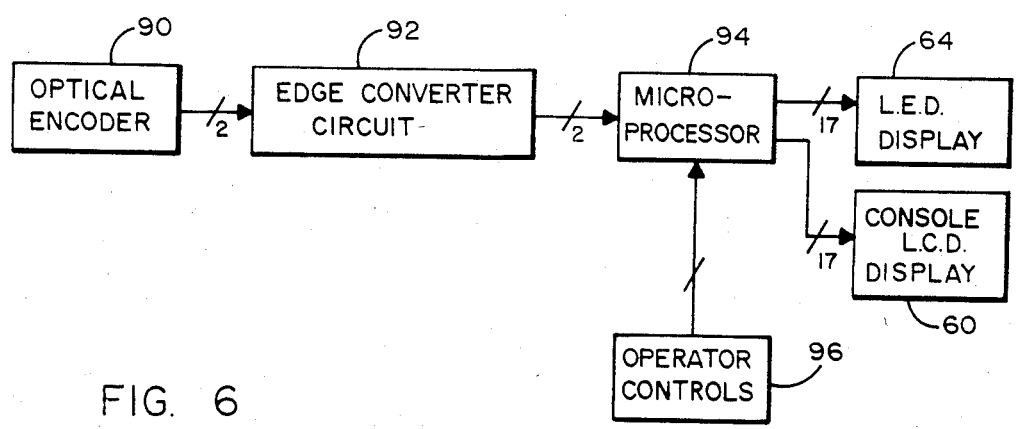
FIG. 6 is a block diagram of the electronics of the optical micrometer.

FIG. 6 illustrates the electronics associated with the optical micrometer. The electronics shown in FIG. 6 are generally conventional. An optical encoder 90 is associated with the cursor 44 to encode the movement of the cursor 44 along a bar pattern in the optical micrometer 40. The movement of the cursor 44 produces quadrature pulses from optical encoder 90 which can be interpreted by an edge converter circuit to provide increased resolution and direction of movement information. The output of the edge converter 92 is in the form of an interrupt to microprocessor 94 which, in effect, algebraically counts the movement increments of the cursor since the last reset. The microprocessor 94 can be reset at any time from the operator control console 60. The y position of the table 22 at the moment of reset then becomes the new zero position of the depth indicator. The control console 60 can also be conventionally arranged to provide brightness control and select desired information.

The digital depth increment count from the microprocessor 94 is applied in a conventional manner to the LED depth indicator 64 (FIG. 5b) and the LCD indicator of control console 60 on the x-y table 22 (FIG. 1).

Although the present invention has been described in connection with the measurement and indication of displacement along the y axis of an x-y table, it will be appreciated that the invention is equally applicable to displacements along any one or more two or three-dimensional rectangular or polar coordinate axes as may be required in any particular type of slit lamp. Likewise, the invention is not restricted to slit lamps, but is equally applicable to other optical devices of the same general construction.

It will be understood that although a specific embodiment of the invention has been described herein, changes can be made in the described embodiment without departing from the spirit of the invention.

We claim:

1. Apparatus for displaying position information in optical instruments, comprising:
   (a) an optical instrument including ocular assembly means for observation of the image of an object;
   (b) coordinate table means for positioning said instrument in the directions of coordinate axes with respect to said object;
   (c) micrometer means including displacement sensing means associated with said coordinate table means and indicating means associated with said instrument for producing data representative of the displacement of said coordinate table means in the direction of at least one of said coordinate axes; and
   (d) display optic means for making an image of said indicator means visible along the periphery of said observed image during said observation.

2. The apparatus of claim 1, further comprising additional indicator means so positioned with respect to said instrument as to be legible without observation of said image, the data indicated by said first-named indicator means and additional indicator means being the same.

3. The apparatus of claim 1, in which said displacement is in the direction of the coordinate axis toward and away from said object.

4. The apparatus of claim 1, further comprising reference setting means for establishing a selectable reference position, said data being algebraically indicative of displacement from said reference position.

5. The apparatus of claim 1, in which said micrometer means include an optical micrometer.

6. The apparatus of claim 1, in which said instrument is a slit lamp including surgical laser means, and said data includes displacement data and data relating to the operation of said laser means.

7. Apparatus for displaying position information in surgical lasers, comprising:
   (a) a surgical laser device;
   (b) coordinate table means supporting said device for movement in the direction of at least one of the coordinate axes; and
   (c) micrometer means including indicator means for producing and indicating data respective of the displacement of the focal plane of the laser beam of said device as a result of the displacement of said device in the direction of at least one of said coordinate axes.

* * * * *